(12) United States Patent
Trog et al.

(10) Patent No.: US 8,849,874 B2
(45) Date of Patent: Sep. 30, 2014

(54) METHOD AND DEVICE FOR ONTOLOGY EVOLUTION

(75) Inventors: Damien Trog, Oudergem (BE); Stijn Christiaens, Zele (BE); Pieter De Leenheer, Brussels (BE); Felix Urbain Yolande Van De Maele, Oostemoe (BE); Robert Alfons Meersman, Deurne (BE)

(73) Assignees: Collibra NV/SA, Brussels (BE); Vrije Universiteit Brussel, Brussels (BE)

( * ) Notice: Subject to any disclaimer, the term of this patent is extended or adjusted under 35 U.S.C. 154(b) by 0 days.

(21) Appl. No.: 13/266,882

(22) PCT Filed: Apr. 27, 2010

(86) PCT No.: PCT/EP2010/055620
§ 371 (c)(1),
(2), (4) Date: Jan. 13, 2012

(87) PCT Pub. No.: WO2010/125061
PCT Pub. Date: Nov. 4, 2010

(65) Prior Publication Data
US 2012/0117023 A1    May 10, 2012

(30) Foreign Application Priority Data
Apr. 30, 2009    (EP) .................................... 09159178

(51) Int. Cl.
G06F 7/00      (2006.01)
G06F 17/30     (2006.01)
G06N 5/02      (2006.01)
G06F 19/28     (2011.01)

(52) U.S. Cl.
CPC .................. *G06N 5/022* (2013.01); *G06N 5/02* (2013.01); *G06F 19/28* (2013.01); *G06F 17/30734* (2013.01)
USPC .............. 707/809; 707/794; 707/798; 706/55

(58) Field of Classification Search
None
See application file for complete search history.

(56) References Cited

U.S. PATENT DOCUMENTS

2003/0172368 A1*  9/2003  Alumbaugh et al. ......... 717/106
2004/0073542 A1*  4/2004  Jones et al. .................... 707/3
(Continued)

FOREIGN PATENT DOCUMENTS

EP          1970844 A2       9/2008

OTHER PUBLICATIONS

Moor et al. "DOGMA-MESS: A Meaning Evolution Support System for Interorganizational Ontology Engineering", Conceptual Structures: Inspiration and Application Lecture Notes in Computer Science; Lecture Notes in Artificial Intellig Ence; LNCS, vol. 4068, Jan. 1, 2006, pp. 189-202.
Meersmann, STARLab Technical Report "Semantic Ontology Tools in IS Design", Esprit Project, "TREVI",nr. 2331, Oct. 22, 2002.
Spyns et al. "Data Modelling Versus Ontology Engineering", ACM Sigmod Record, vol. 31. No. 4, pp. 12-17 Dec. 31, 2002.

(Continued)

*Primary Examiner* — Dung K Chau
(74) *Attorney, Agent, or Firm* — Workman Nydegger

(57) ABSTRACT

A method for modifying a mapping from at least one application path of a data system to a conceptual path of an ontology system is provided. The application path addresses a part of the structure of the data system, and the conceptual path addresses a part of the structure of the ontology system. The method comprises the steps detecting a change to a part of the structure of the ontology system one or more of the conceptual paths is addressing and updating the mappings to reflect the change to the part of the structure of the ontology system.

11 Claims, 6 Drawing Sheets

(56) References Cited

U.S. PATENT DOCUMENTS

| | | |
|---|---|---|
| 2006/0036633 A1* | 2/2006 | Chong et al. ............... 707/101 |
| 2006/0129843 A1* | 6/2006 | Srinivasa et al. ........... 713/189 |
| 2006/0129905 A1* | 6/2006 | Spork ......................... 715/500 |
| 2007/0162409 A1* | 7/2007 | Godden et al. .............. 706/48 |
| 2007/0198448 A1 | 8/2007 | Fokoue-Nkoutche et al. |
| 2007/0299799 A1* | 12/2007 | Meehan et al. ............. 706/46 |
| 2008/0071731 A1 | 3/2008 | Ma et al. |
| 2008/0215542 A1* | 9/2008 | Lim et al. .................... 707/3 |
| 2008/0256121 A1* | 10/2008 | Liu et al. ..................... 707/102 |
| 2008/0295068 A1* | 11/2008 | Kendall et al. ............. 717/104 |
| 2009/0094216 A1* | 4/2009 | Hou et al. .................... 707/4 |

OTHER PUBLICATIONS

Spyns et al. "Object Role Modelling for Ontology Engineering in the DOGMA framework", On the Move to Meaningful Internet Systems, OTM Workshop Lecture Notes, vol. 3762, pp. 710-719, Jan. 1, 2005.
Wang et al., "An Ontology Data Matching Method for Web Information Integration", iiWAS 2008, Nov. 24-26, 2008, pp. 208-213.
International Search Report in PCT/EP2010/055620, Apr. 1, 2011.
European Office Action issued in EP10717615.8, dated Jan. 22, 2013.

\* cited by examiner

BEFORE CHANGE | AFTER CHANGE

RELABEL:

APPEND:

INSERT:

DELETE:

METHOD AND DEVICE FOR ONTOLOGY EVOLUTION

FIELD OF THE INVENTION

The present invention generally relates to ontology engineering. More particularly, the present invention relates to ontology evolution and maintenance of changes within ontology systems.

BACKGROUND OF THE INVENTION

Internet and other open connectivity environments create a strong demand for sharing the semantics of data. Ontology systems are becoming increasingly essential for nearly all computer applications. Organizations are looking towards them as vital machine-processable semantic resources for many application areas. An ontology is an agreed understanding (i.e. semantics) of a certain domain, axiomatized and represented formally as logical theory in the form of a computer-based resource. By sharing an ontology, autonomous and distributed applications can meaningfully communicate to exchange data and thus make transactions interoperate independently of their internal technologies.

Ontologies capture domain knowledge of a particular part of the real-world, e.g., knowledge about product delivery. Ontologies can be seen as a formal representation of the knowledge by a set of concepts and the relationships between those concepts within a domain. Ontologies must capture this knowledge independently of application requirements (e.g. customer product delivery application vs. deliverer product delivery application). Application-independence is the main disparity between an ontology and a classical data schema (e.g., EER, ORM, UML) although each captures knowledge at the conceptual level. For example, many researchers have confused ontologies with data schemes, knowledge bases, or even logic programs. Unlike a conceptual data schema or a "classical" knowledge base that captures semantics for a given enterprise application, the main and fundamental advantage of an ontology is that it captures domain knowledge highly independent of any particular application or task. A consensus on ontological content is the main requirement in ontology engineering, and this is what mainly distinguishes it from conceptual data modelling.

The research area of ontology engineering seems to have reached a certain level of maturity, considering the vast amount of contemporary methods and tools for formalising and applying knowledge representation models. However, there is still little understanding of, and support for, the evolutionary aspects of ontologies. This is particularly crucial in distributed and collaborative settings where ontologies naturally co-evolve with their communities of use. For managing the evolution of single ontologies, established techniques from data schema evolution have been successfully adopted, and consensus on a general ontology evolution process model seems to emerge.

Much less explored, however, is the problem of evolution of interorganisational ontologies. In this "complex" and dynamic setting, a collaborative change process model requires more powerful engineering, argumentation and negotiation methodologies, complemented by support for context dependency management. It turns out that much can be learned from other domains where formal artifacts are being collaboratively engineered. In particular, the field of system engineering offers a wealth of techniques and tools for versioning, merging and evolving software artifacts, and many of these techniques can be reused in an ontology engineering setting. The key remaining challenge is to construct a single framework, based on these mechanisms, which can be tailored for the needs of a particular version environment.

Ontologies often reuse and extend (parts of) other ontologies. Many different types of dependencies exist within and between ontological artifacts of various levels of granularity, ranging from individual concepts of definitions to full ontologies. Other dependent artifacts include instances, as well as application programs committing to the ontology. Hence, a change on request in one artifact might imply a cascade of changes in response to all its dependent artifacts. A viable method is needed to log all implications to the ontology and its dependent artifacts.

EP1970844 describes a method for metamodeling using dynamic ontology objects. So called "ontology objects", i.e. sets of software interfaces and implementations, are updated based on changes in a metamodel: when a change has been made to the metamodel, the ontology objects are updated by generating new source code. A problem herewith is that the change is made on the level of the ontology objects. There is no mapping between ontology model and metamodel. It remains difficult for a participating application to detect and apply corresponding changes to the interface between application and ontology objects.

The same problem occurs in US2007/162409, where a command is received from a requestor to modify a table including domain concepts and semantic primitives related to a domain. The table is updated in response to the command. The updated table is then stored as an ontology.

In the paper "*Dogma-Mess: A Meaning Evolution Support System for Interorganizational Ontology Engineering*" (A. De Moor et al., Conceptual Structures: Inspiration and Application Lecture Notes in Computer Science, vol. 4068, 1 Jan. 2006, pp. 189-202) a model for interorganisational ontology engineering is introduced. The paper is limited to describing the evolution of an ontology system based on a set of specialisations on this ontology, the latter called organisational ontologies. It does not describe evolution operators in great detail. More importantly, it does not consider applications mapped on the ontology system. In other words it does not describe how to evolve the mappings between application paths in an arbitrary data system and conceptual paths in an ontology system based on the changes applied to that ontology system. The paper mentions versioning and change operations, but does not describe this in a formal and detailed way.

"*Data Modelling versus Ontology engineering*" (P. Spyns et al., ACM Sigmod Record, vol. 31, no. 4, pp. 12-17, 31 Dec. 2002) describes the difference between a data model and an ontology as perceived by the authors, and introduces the DOGMA ontology approach. It does not describe evolution of ontologies, nor does it describe how to evolve the mappings of application paths in an arbitrary data system to conceptual paths in an ontology system based on the changes applied to that ontology system.

In "*Object Role Modelling for Ontology Engineering in the DOGMA Framework*" (P. Spyns et al., On the Move to Meaningful Internet Systems 2005, OTM Workshop Lecture Notes, vol. 3762, pp. 710-719, 1 Jan. 2005). This paper is limited to a description of some basic issues to be taken into account when using the ORM methodology for ontology engineering from the DOGMA ontology framework point of view. First it discusses the difference between a data model and ontology. Further it discusses natural and formal semantics. Finally, the paper discusses some basic steps to be taken when constructing ontologies. The paper does not touch upon the topics of evolution or versioning.

There is a need to maintain and apply changes to an ontology system at the level of the interface between application and ontology system. This is especially needed when multiple applications are linked to the same ontology system. Adapting for changes may otherwise be a very elaborate job.

Aims of the Invention

The present invention aims to provide a method and system for flexible ontology evolution, whereby one can keep track of the changes within the ontology system.

SUMMARY OF THE INVENTION

The present invention proposes updating mappings from application paths in a data system to conceptual paths in an ontology system based on detected changes to that ontology system. It is to be noted that, unlike the ontology objects in prior art solutions (e.g. EP1970844), the data system in this invention does not have to be changed during the process, only the mappings are changed. An ontology system is considered to which is linked a data system used by a computer application. The ontology has a certain syntactic structure, wherein conceptual paths are defined. The data system has a structure addressable by application paths. A situation is considered wherein a change has been made to the ontology system.

More specifically, the present invention provides a method for modifying a mapping from at least one application path of a data system to a conceptual path of an ontology system, said application path addressing a part of the structure of the data system and said conceptual path addressing a part of the structure of the ontology system. The method comprises the steps of:
- detecting a change to a part of the structure of the ontology system that one or more of the conceptual paths is addressing;
- updating the mappings to reflect the change to that part of the structure of the ontology system.

Some examples of changes often occurring in an ontology (like, e.g., relabel, append, insert, delete) are given below.

In a preferred embodiment the detected change is stored in a change log. Such a change log keeps track of the various changes to the ontology system when going from one version to a successor version.

In one embodiment the method comprises an initial step of applying said change to the ontology system. This is a typical situation: first a change is made to a part of structure of the ontology system in question. Next, said change must be detected and the mappings need an update. In an embodiment one or more conditions are imposed for applying said change.

A change to (a part of) the ontology system structure may constitute a single change or a set of various changes. In one embodiment the change comprises a relabeling of part of the ontology system structure. The change may also be appending another structure to part of the ontology system structure, said other structure not being part of the ontology system structure before the change. The change comprises inserting a further structure to a part of the ontology system structure, whereby that further structure is not part of the ontology system structure before the change. The change may also comprise the deletion of part of the structure of the ontology system.

In another aspect a program is provided executable on a programmable device containing instructions, which, when executed, perform the method as set out above.

In a further aspect a device is provided for modifying a mapping from at least one application path of a data system to a conceptual path of an ontology system, whereby the application path addresses a part of the structure of said data system and the conceptual path addresses a part of the structure of the ontology system. The device comprises means for detecting a change to a part of the structure of the ontology system one or more of the conceptual paths is addressing and means for updating the mappings to reflect the change to the part of the structure of the ontology system. Combinations of these possible changes can occur as well, as the skilled person will appreciate.

In a preferred embodiment the device is arranged for identifying and storing information on the version of the ontology system.

DETAILED DESCRIPTION OF THE INVENTION

Figure 1:
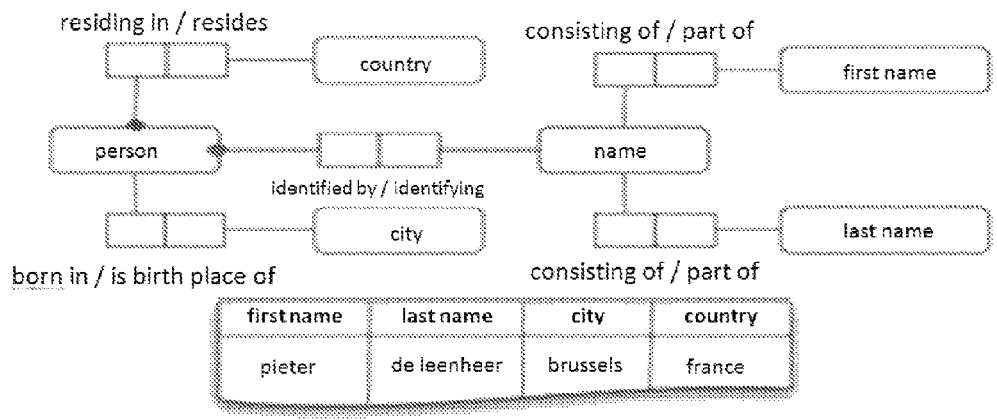
FIG. 1 illustrates on top a semantic pattern that could be useful to annotate the logical data schema on the bottom of the figure.

Ontologies in general define shared representations for two essential and dual aspects of semantics of a domain, i.e. a formal semantics for information allowing information processing by a computer, and a real-world semantics allowing linking machine processable content with meaning for humans based on consensual terminologies and natural language.

The ontology representation approach introduced in the present invention adopts a fact-oriented modelling approach. In this approach facts are considered the unit of communication and hence build representations for semantics from abstracting these observed facts into fact types. Facts represent objects (entities or values) playing a certain role (part in relationship). This is different from attribute-based approaches such as object-oriented modelling where the domain is represented by abstracting data types from observed objects.

A data system is defined by the combination of an intentional and extensional part. Its intentional definition prescribes the constraints data elements in the form of data types (e.g., integers, strings) and relationships between them (e.g., multiplicity). An extensional definition prescribes which data elements belong to which data types. A data system can be annotated by an ontology and can be regarded as an application committing to the ontology. An application commits to an ontology system if the data system it is using, maps on the ontology system. Such a mapping is performed by mapping application paths that address a part of the structure of the data system. An example of a data system is a relational database. In a relational database an example of an application path would address a particular attribute in a particular table. The intentional part is defined by its schema. The extensional part is defined by its population. Other examples of data systems include XML and its corresponding schema, EDI messages, etc. The ontology system can also handle data systems for which the intentional part is not available e.g., XML having no corresponding schema. For example, in an XML file an application path could be an XPath.

The ontology system separates the representation of domain semantics and the annotation of the application with these semantics in three separate layers: Lexon Base, Pattern Base, Commitment Layer.

A lexon is a quintuple that defines a plausible binary fact type within a certain context. The quintuple is defined as {Context, Head-term, Role, Co-role, Tail-term}. The role, and its reverse co-role, defines the conceptual relation between the head and tail term. Intuitively a lexon may be read as: within the context, the head term may have a relation with the tail term in which it plays a role, and conversely, in which the tail term plays a corresponding co-role.

A context in a lexon provides a reference to one or more lexical resources and/or parts of a lexical resource (such as documents) from which the lexon was elicited. Contexts are important to prevent lexical ambiguity of terms within lexons, as the meaning of terms may vary according to the context.

Lexons as such do not have a reading direction, however when constructing a path it can be given one out of two directions by either starting with the head term or tail term.

A lexon base is defined as a set of lexons. The goal of the lexon base is to provide a shared and evolving resource that is used to reach a common and agreed understanding about the ontology vocabulary and is thus aimed at human understanding, associating natural language terms. The lexon base reflects the syntactic structure of the ontology system.

A conceptual path in a lexon base is defined by a context-term pair or a finite concatenation of lexons in that lexon base. In the latter case it also imposes a particular reading direction. A conceptual path may be a single concept (e.g., Delivery), a lexon (e.g., Date of Delivery) or a grouping of different lexons (e.g., Day of Date of Date and Time of sending Delivery). Hence, conceptual paths are capable of addressing parts of the structure of the ontology system. Conceptual paths are used in patterns to define semantic constraints and in commitments to define mappings.

A semantic pattern is defined by a meaningful selection of conceptual paths in a particular lexon base plus a set of semantic constraints. Each semantic constraint has certain type and is expressed as a collection of sets of conceptual paths. FIG. 1 illustrates a semantic pattern in the ORM notation. It includes many different conceptual paths. E.g., from bottom right term Last Name to the upper left term Country, we verbalise the conceptual path: Last name part of Name identifying Person residing in Country. A pattern base is defined by a set of semantic patterns.

A commitment from a computer application to an ontology system is defined by a selection of semantic patterns part of the lexon base in the ontology system, a set of semantic constraints on these patterns and a set of mappings that map from the data system used by the application to the ontology system. More precisely, the application paths of the data system are mapped to conceptual paths in these patterns. The commitment layer is defined by the set of all commitments.

Each individual commitment within the commitment layer is a representation of the semantics of a specific data system in terms of the lexon base. Patterns can be reused across commitments if they are selected from the same pattern base. Doing so, the ontology system establishes semantic interoperability between data systems and applications in general (e.g., software agents and web services).

Rules constrain and attribute specific interpretations to a selected subset of patterns contained within the pattern base, e.g., each Person has at least one address. As such each individual commitment rule represents the semantics of a specific application.

Figure 2:
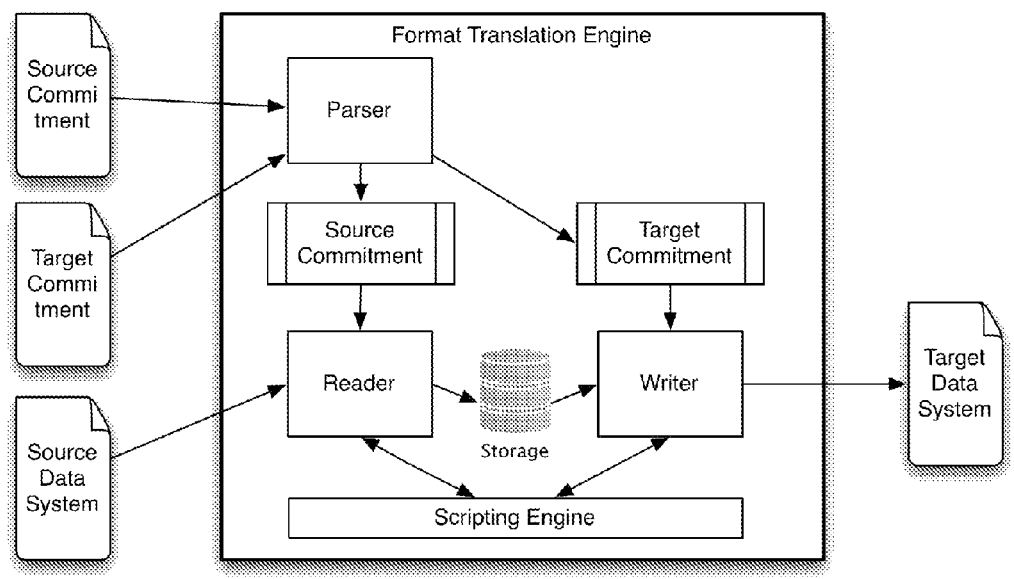
FIG. 2 represents an overview of inputs and outputs of the translation engine.

Application paths addressing part of the structure of the data system are mapped onto conceptual paths. Mappings are required to automatically create data value transformations between a structured data system and a structured ontology system. Given a source data system and a target data system, and their respective mappings to a shared part of an ontology system, it is possible to automatically create data value transformations between said source and target data systems. The transformation is automatically done by a translation engine. The translation engine works by parsing a source and target commitment, which contain the mappings of application paths from a data system onto conceptual paths from an ontology system, and read data symbols from the source data system and write the translated symbols into the target data system. FIG. 2 gives an overview of inputs and outputs of the translation engine. The engine itself is componentized into:

- a parser that builds a syntax tree from a textual commitment,
- a reader that takes care of querying a data system,
- a writer that takes care of updating and creating data in a data system,
- a scripting engine accessible by the reader and writer.

Custom scripts can be written by users of the engine that allow modification of the runtime behavior without changing the engine itself. The translation engine uses a push and pull approach depending on the kind of data system.

Push Approach

In the push approach the Reader starts reading the source data system and pushes the data symbols into the storage system, which are immediately taken up by the Writer and written into the target data system. In effect the Source Data System is pushing its data into the Target Data System. The push approach is used for tree-structured source data systems, such as XML. In the source commitment the mappings are processed in the order that they are listed. The first mapping is assumed to point to the root element. The mappings should be in the following form:

```
map "/a" on A.
map "/a/b" on B of A.
map "/a/b/c" on C of B of A.
map "/a/d" on D of A.
```

The 'map' keyword indicates that this statement is a mapping. The left part of the mapping is an application path expressed in a path language that can be used to address elements in the data system (e.g., XPath). The application path is enclosed in double quotes.

The application path contains enough information to construct a query processable by a query engine that supports the data format of the data system. The Reader sends these queries to the appropriate query engine. For example in XML, XPaths can be processed as queries by an XPath engine like Xalan. The same application path is also used by the Writer to write data to the location the path addresses.

The 'on' keyword separates the left and right parts of the mapping statement. On the right a conceptual path is written, constructed using symbols from the ontology system. Each statement ends with a dot.

Mappings are processed in the given order. The conceptual paths are related to each other by this order. In the above example the instance for the A concept is the same in each of the mappings. We know this because the first element in the application path is also the same and because it is pointing to the root element. Other non-root elements can be repeated and the corresponding concept is instantiated every time. For example when there are three b elements, three corresponding B concepts are instantiated. For each of the mappings zero or more conceptual paths can be instantiated, depending on the number of elements in the source data system.

Following is an example XML that is valid for the above mappings.

```
<a>
    <b>
        <c>text</c>
    </b>
    <b>
        <c>text2</c>
    </b>
    <b>
        <c>text3</c>
    </b>
</a>
```

This instantiates the following paths (the instances of concepts are between parentheses, where entities are identified by a number prefixed with the @ symbol, and values are shown between double quotes):

```
A(@1).
B(@1) of A(@1).
B(@2) of A(@1).
B(@3) of A(@1).
C("text") of B(@1) of A(@1).
C("text2") of B(@2) of A(@1).
C("text3") of B(@3) of A(@1).
```

The writer uses the reverse of this process and constructs the data for the target data system from these instantiated paths.

The writer looks up which mapping corresponds to the instantiated path and constructs the elements in the data system.

Pull Approach

Alternatively, a pull approach lets the Writer decide which data it needs from the Reader. In this case, the Writer asks the Reader for each piece of data it needs. The writer is pulling the data from the reader, which puts it in the storage, ready for the Writer to access. The pull approach is used for graph based data systems, such as relational databases. As opposed to the push approach, the pull approach starts with the writer that requesting instantiated paths from the reader for its mappings.

Given an ontological commitment conceptual queries are executed on any data system that is correctly annotated by that commitment. A conceptual query is a language construction expressed in terms of one or more conceptual paths in a commitment. Given the mappings between conceptual paths and application paths in a commitment, the conceptual queries can be executed as logical queries in the committing data system. This is done by translating (the conceptual paths in) the conceptual query into a logical query in terms of the application paths of the data system. A logical query is a query within the data system. For example, a logical query on a relational database would be expressed in SQL.

In one embodiment ontological commitments are specified in the Ω-RIDL (Omega-RIDL) controlled natural language. The language describes semantic rules in terms of conceptual paths in which role- and co-role-labels need to be interpreted as an ontological relationship. Ω-RIDL is both a conceptual query and commitment specification language.

The systems and methods of the invention may be seen as a further improvement of the DOGMA approach for developing ontology-guided mediation of agents. DOGMA (R. Meersman., Proc. of the International Symposium on Methodologies for Intelligent Systems (ISMIS), pp. 30-45, 1999) is an ontology approach and framework that is not restricted to a particular representation language. Embodiments of the present invention apply the DOGMA framework for ontology based data mapping.

Figure 3:
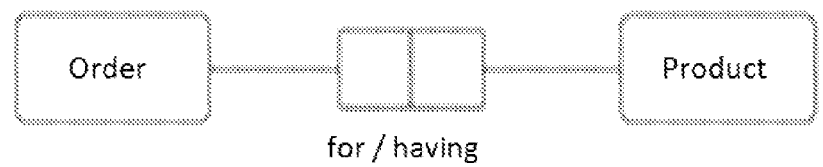
FIG. 3 illustrates a fact-type that can be traversed in two directions, denoting two paths.

FIG. 3 illustrates a relationship between two concepts Product and Order. Each lexon can be traversed in two directions, denoting two paths: an Order for a Product, and a Product having an Order.

Conceptual paths can be concatenated to form composite paths. These concatenations can be further formalised with rules and constraints, restricting the possible use of the concepts and relationship in the ontology.

The annotation is expressed in Ω-RIDL. FIG. 1 illustrates on top a semantic pattern that could be used to annotate the logical data schema on the bottom of the figure.

Each relevant symbol in the logical data schema instance is annotated by a meaningful conceptual path in the pattern. If a relevant symbol cannot be annotated by the current pattern version, the pattern is changed in such a way that the new pattern version allows annotating the pending symbols.

In the example above, all attributes in table People (the application paths) can be mapped on conceptual paths in the pattern. Hence, one can read out:

map "People.firstname" on "First Name part of Name identifying Person"
map "People.lastname" on "Last Name part of Name identifying Person"
map "People.city" on "City is birth place of Person"
map "People.country" on "Country resides Person"

The example above is trivial, as the terms for the attribute symbols are intuitively interpretable. However in real-world scenarios the meaning of the symbols in the logical schema is usually implicit. Even in this example: although the independent meanings of the symbols city, country and person are intuitively obvious, their inter-relation is not. Country and city appear to be not related at all, as can also be inferred from the attribute values. On the other hand, first name and last name appear to be related to each other indirectly via the meronymical (part-of) relationship with name.

The above annotation system works for different types of data management technology, including relational tables and columns, object-oriented classes, or XML tags. Given a shared ontology, queries in one annotated logical data schema can be automatically translated to queries in any other logical data schema that is annotated with this ontology. Hence, this provides a universal approach to data integration. Furthermore, as the annotations are close to natural language, the meaning of symbols in the schemas can be described and interpreted by the layman end user.

Evolution

Implementing a change to an ontology system is a difficult process that necessitates many different sub-activities: change propagation, restructuring and inconsistency management.

For this purpose the device according to the present invention comprises in a preferred embodiment a versioning layer. Said versioning layer provides all the functionality for identifying and storing ontology versions and change logs. Change logs keep track of the changes required to determine one version of the ontology system starting from an older version. An ontology editor may support the versioned editing of ontologies with a graphical interface.

All information about the performed changes are tracked and recorded in a change log, also referred to as a version log. A change log between an ontology system version K and an ontology system version K-F1 is defined as a sequence of change operations that was performed on version K, in order to result in version K+1.

Figure 4:
FIG. 4 illustrates a change comprising a relabeling, appending, insertion and deletion, respectively.
Figure 4:
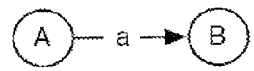
Figure 4:
Figure 4:
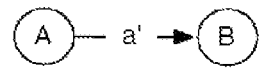
Figure 4:
Figure 4:
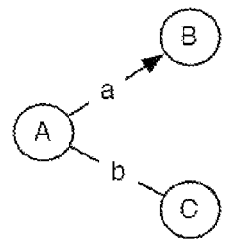
Figure 4:
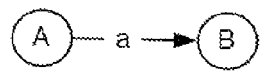
Figure 4:
Figure 4:
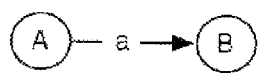
Figure 4:

Examples of changes at the lexon base level are relabeling, inserting or appending lexons to or removing lexons from the existing ontology system structure. Examples of change operators on the pattern base level are create or remove pattern. Examples of change operators on the commitment layer level are create, revise or remove path or rule. This is illustrated in FIG. 4. The figure shows from top to bottom four types of changes that can occur in an ontology system. Relabel type includes any renaming of a term for a concept (node) or relationship (edge) in the ontology system. In the first example, before the change a concept is referred to by a term 'B'. After the change the same concept is referred to by a term 'B'''. In the second example, the relationship referred to by 'a' between concepts (referred to by terms 'A' and 'B') gets a new term 'a''.

Append type includes any change that attaches a new structure of the existing ontology system. For example, before the change, part of the ontology system consists of a concept referred to by term 'A'. After the change a new structure including concepts referred to by terms 'B' and 'C' and relationships referred to by 'a' and 'b' respectively are appended to this existing concept.

Insert type includes any change that inserts a new structure in between two existing parts of the ontology system. For example, here a new concept referred to by term 'B' and relationship referred to by 'c' is inserted in between existing concepts 'A' and 'C'. The insert type is applied in the examples Move Relation, Conceptify, Short Circuit discussed below.

Delete type includes any change that removes a part of the structure of the ontology system. For example, removing a relation referred to by term 'a' between concepts 'A' and 'B'.

Updating Mappings Based on Changing the Ontology System

A mapping of a data system to an ontology system version K might become broken when changing ontology system version K to version K-F1, because the conceptual paths used in the mapping are restructured, deleted or deprecated. Therefore any mapping with ontology system version K should be adapted to the new ontology system version K+1. The change log stores the sequence of all operations (changes) between two ontology system versions. The change log can thus be used for different purposes such as to identify conflicts or meaning divergences. In the example above, changing symbol "Person" to "Individual" triggers a change to the mapping in which Person was involved:

map "People.firstname" on "First Name part of Name identifying Individual"

map "People.lastname" on "Last Name part of Name identifying Individual"

map "People.city" on "City is birth place of Individual"

map "People.country" on "Country resides Individual"

Using the change log other conflicts can be identified when merging parallel evolutions of one ontology version. For each of the conflicts, the present invention provides a set of alternative resolution strategies.

Deriving a Set of Reusable Patterns in the Ontology

Given a set of similar ontologies, the common parts can be collected and automatically abstracted into patterns that can be reused for later purposes. For example, different organisations may reuse independently the concept pattern for a job task for annotating their data schemas about delivery.

A change log is a transcript of an ontology evolution process that is represented by an ordered sequence of ontology operations. Each change log is restricted to operations from some particular operator classes. Some operators have pre- and post-conditions and each operator belongs to an operator class. Also failed operations are logged, including the unsatisfied conditions that caused the failure.

An atomic ontology evolution operator C defines the semantics of change of an ontology in terms of the following properties: a precondition PreCond(C) for a change operator C is a condition that must hold in an ontology O in order for C to be applicable to that ontology O, and a postcondition PostCond(C) for a change operator C is a condition that must hold in an ontology O' that is the result of applying C to ontology O.

A compound ontology evolution operator is defined by an ordered sequence of atomic ontology evolution operators. An ontology evolution operation is a specific occurrence of an ontology evolution operator.

In the present invention provides changes are detected to the annotation of one or more information systems, said changes comprising a set of compound operators grouping a number of atomic operators for the semantic patterns and equivalent operators for the mappings in the commitments, wherein said compound operators are added to the change log.

In what follows specific embodiments of change operations and operators are explained by means of examples. Other sets of operators may be received by the change log to provide a sequence of changes. Each of the operators is a variation of the above mentioned types of changes: relabel, insert, append and delete.

For the reader's convenience, header and tail term start with a capital case, and role/co-role terms are in small case.

Example 1

Refining Concepts

In an embodiment said compound operators comprise atomic operators for refining concepts and acting on the conceptual path part of the corresponding mappings. Refining is an example of the append type.

Figure 5:
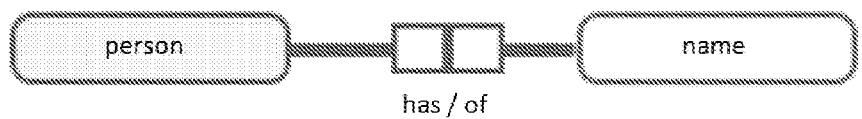
FIG. 5 illustrates a simple semantic pattern to express that persons can have names.
Figure 6:
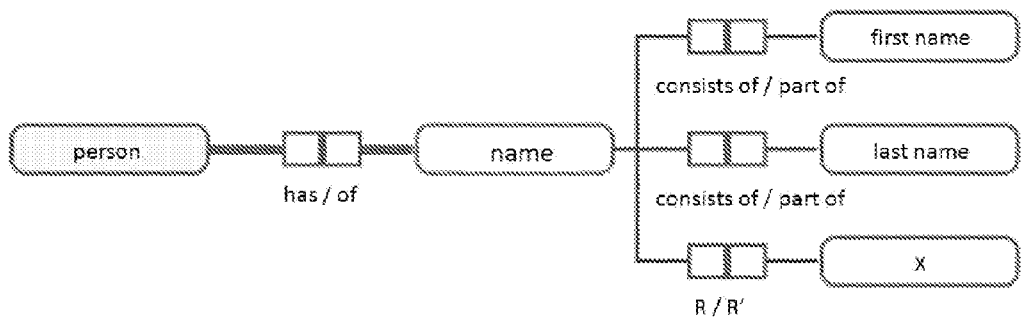
FIG. 6 illustrates the semantic pattern of FIG. 5 after applying a change log for refining the name concept.

Consider the example illustrated in FIGS. 5 and 6. FIG. 5 displays a simple semantic pattern to express that persons can have names. This is mapped to an example XML using the following Ω-RIDL expressions:

> map "concat(/person/pname/fname, /person/pname/lname)"
> on Name of Person.

Because the semantic pattern is too limited to express the information of e.g. a new business partner, it must be expanded to also include first and last names explicitly. This can be achieved using the following change log:

> introduceTerm("First Name")
> defineDifferentia("Name", "consists of", "part of", "First Name")
> introduceTerm("Last Name")
> defineDifferentia("Name", "consists of", "part of", "Last Name")
> ...
> introduceTerm(X)
> defineDifferentia("Name", r, r', X)

Applying these operations on the semantic pattern of FIG. 5 arrives at the semantic pattern of FIG. 6. This semantic pattern requires a new commitment with the following mappings replacing the previous ones:

> map "/person/pname/fname"
> on First Name part of Name of Person.
> map "/person/pname/lname"
> on Last Name part of Name of Person.
> ...
> map "/person/pname/xxx"
> on X r' Name of Person.

The solution provided by the present invention is firstly the introduction of a compound operator for the semantic pattern that can be incorporated in the change log. The compound operator defines a specific sequence of atomic operators. Secondly, this compound operator needs to have an equivalent operator that operates on the mappings in the commitment(s).

The new operator may be defined as follows:

$refine(X, r, r', Z_1, \ldots Z_n) \equiv$ $+ introduceTerm(Z_1) + defineDifferentia(X, r, r', Z_1) +$ $\ldots + introduceTerm(Z_n) + defineDifferentia(X, r, r', Z_n)$ Applied on the example, this gives the following compound operator for the semantic pattern in the change log:

$refine$("Name", "consists of", "part of", "First Name",

"Last Name", "X") $\equiv + introduceTerm$("First Name") +

*defineDifferentia*("Name", "consists of", "part of", "First Name") +

*introduceTerm*("Last Name") +

*defineDifferentia*("Name", "consists of", "part of", "Last name")

$\ldots + introduceTerm("X") +$

*defineDifferentia*("Name", "consists of", "part of", "X")

Concerning the mappings, the operator acts on the conceptual path part of the mappings:

> map "concat(/person/pname/fname, /person/pname/lname)"
> on Name of Person.

The operator expresses that this conceptual path has been refined and asks the user how to perform the refinement:

> map "/person/pname/fname"
> on $Z_1 \ldots Z_n$ ? r' Name of Person.
> map "/person/pname/lname"
> on $Z_1 \ldots Z_n$ ? r' Name of Person.

Note that the operator only allows the refinement using the same relation, i.e. in the case of the example: consists of/part of. A multitude of "refine" operators may be applied, e.g. "split" and "attribute".

Note also that the XML application path in this example is an aggegrate function (concat). The algorithm used can identify these and therefore split them up nicely in separate mappings (based on the "refine" operator).

Example 2

Rolifying Concepts

In another embodiment the compound operators comprise atomic operators for distributing the semantics over both terms and roles. This is an example of the relabel type.

Figure 7:
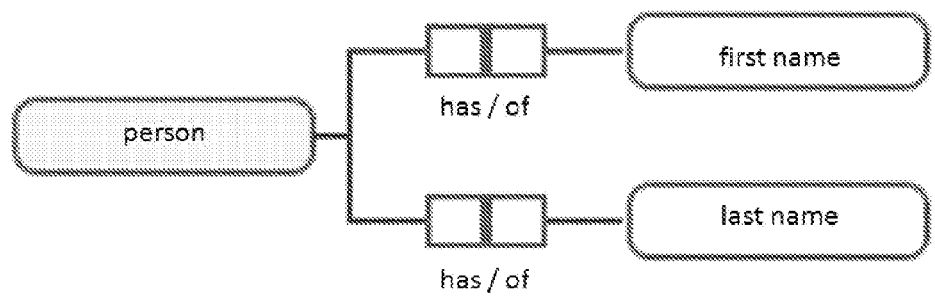
FIG. 7 illustrates a semantic pattern to express that persons can have first and last names.
Figure 8:
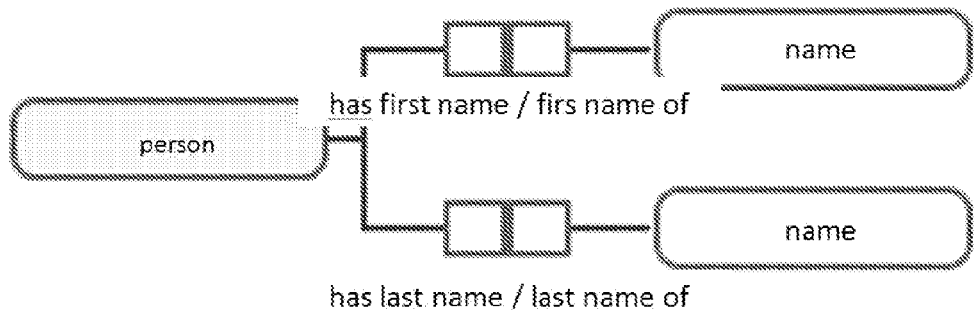
FIG. 8 illustrates the semantic pattern of FIG. 7 after applying a change log for distributing the semantics over both terms and roles.

Consider the example illustrated in FIGS. 7 and 8. FIG. 7 describes the semantic pattern as is. The corresponding mapping is as follows:

> map "/person/name/fname"
> on First Name of Person.
> map "/person/name/lname"
> on Last Name of Person.

Because it is preferred to distribute the semantics over both terms and roles, the semantic pattern needs to evolve using the following change log:

> defineDifferentia("Person", "has first name", "first name of", "Name")
> dropDifferentia("Person", "has", "of", "First Name")
> defineDifferentia("Person", "has last name", "last name of", "Name")
> dropDifferentia("Person", "has", "of", "Last Name")

This results in the pattern of FIG. 8, and should result in updated mappings in the commitment as follows:

```
map "/person/name/fname"
  on Name first name of Person.
map "/person/name/lname"
  on Name last name of Person.
```

The solution provided by the present invention is firstly the introduction of a compound operator for the semantic pattern that can be incorporated in the change log. The compound operator defines a specific sequence of atomic operators. Secondly, this compound operator needs to have an equivalent operator that operates on the mappings in the commitment(s). The new operator is defined as follows:

$$rolify(X, r', r, Y, a', a) \equiv +defineDifferentia(X, a', a, Y) +$$
$$dropDifferentia(Y, r', r, X) \text{ or } rolify(X, r', r, Y) \equiv$$
$$+rolify(X, r', r, Y, \text{"X of"}, \text{"has X"})$$

Applied on the example, this gives the following element in the change log:

$rolify(\text{"First Name"}, \text{"of"}, \text{"has"}, \text{"Person"},$

"first name of", "has first name") + *defineDifferentia*

("*Name*", "first name of", "has first name", "Person") +

*dropDifferentia*("First Name", "of", "has", "Person")

or *rolify*("First Name", "of", "has", "Person") ≡

+*defineDifferentia*("Name", "first name of",

"has first name", "Person") +

*dropDifferentia*("First Name", "of", "has", "Person")

Concerning the mappings, the operator acts on the conceptual path part of the mappings:

```
map "/person/pname/fname"
  on First Name of Person.
```

The operator expresses that this conceptual path has been rolified, and performs the operation

```
map /person/name/fname
  on Name first name of Person
```

Figure 9:
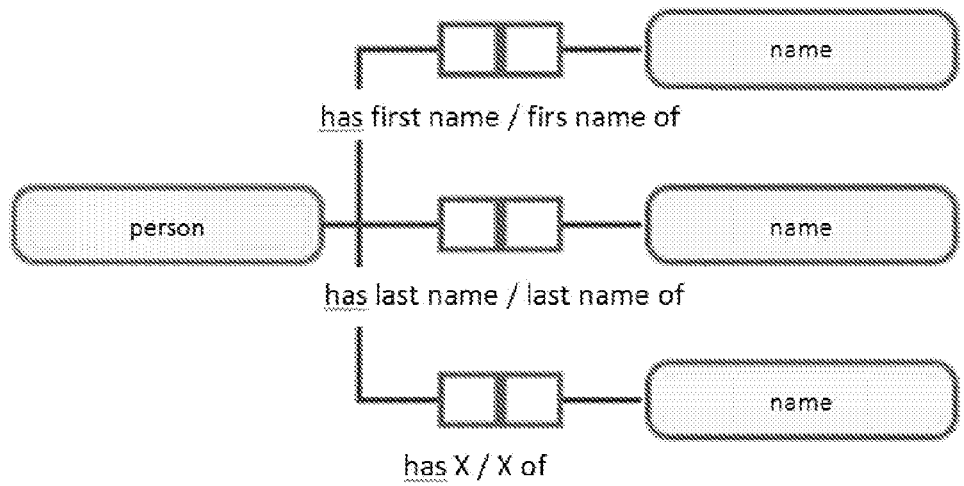
FIG. 9 illustrates the semantic pattern of FIG. 6 after applying a change log for distributing the semantics over both terms and roles.

Consider another example illustrated in FIGS. 6 and 9. FIG. 6 describes the semantic pattern as is. The corresponding mapping is as follows:

```
map "/person/name/fname"
  on First Name part of Name of Person.
map "/person/name/lname"
  on Last Name part of Name of Person.
map "/person/name/xxx"
  on X r' Name of Person.
```

Because it is preferred to distribute the semantics over both terms and roles, the semantic pattern needs to evolve using the following change log:

defineDifferentia("Person", "has first name", "first name of", "Name")
dropDifferentia("Name", "consists of", "part of", "First Name")
defineDifferentia("Person", "has last name", "last name of", "Name")
dropDifferentia("Name", "consists of", "part of", "Last Name")
defineDifferentia("Person", "has X", "X of", "Name")
dropDifferentia("Name", r, r', X)
dropDifferentia("Person", "has", "of", "Name")

This results in the pattern of FIG. 9, and should result in updated mappings in the commitment as follows:

```
map "/person/name/fname"
  on Name first name of Person.
map "person/name/lname"
  on Name last name of Person.
map "/person/name/xxx"
  on Name X of Person.
```

The solution provided by the present invention is firstly the introduction of a compound operator for the semantic pattern that can be incorporated in the change log. The compound operator defines a specific sequence of atomic operators. Secondly, this compound operator needs to have an equivalent operator that operates on the mappings in the commitment(s). The new operator is defined as follows:

$$rolify(X, r', r, Y, a', a, Z) \equiv +defineDifferentia(Z, \text{"has } X\text{"}, \text{"}X \text{ of"}, Y) +$$
$$dropDifferentia(Y, r', r, Z)[+dropDifferentia(Z, a, a', Y)]$$

Applied on the example, we get the following element in the change log:

+*rolify*("First Name", "part of",

"part of", "Name", "of", "has", "Person") ≡

+*defineDifferentia*("Person", "has first name",

"first name of", "Name") +

*dropDifferentia*("Name", "consists of", "part of", "First name")

[+*dropDifferentia*("Person", "has", "of", "Name")] +

*rolify*("Last Name", "part of", "part of",

"Name", "of", "has", "Person") ≡

+*defineDifferentia*("Person", "has last name", "last name of",

"Name") + *dropDifferentia*("Name", "consists of",

"part of", "Last Name")[+*dropDifferentia*("Person",

"has", "of", "Name")] + *rolify*("X", "part of",

"part of", "Name", "of", "has", "Person") ≡

+*defineDifferentia*("Person", "has X", "X of", "Name") +

*dropDifferentia*("Name", "consists of", "part of", "X")

[+*dropDifferentia*("Person", "has", "of", "Name")]

Concerning the mappings, the operator acts on the conceptual path part of the mappings:

map "/person/pname/fname"
on First Name part of Name of Person.

The operator expresses that this conceptual path has been rolified, and performs the operation map "/person/name/fname"
on Name first name of Person.

Example 3

Moving Relations

Figure 10:
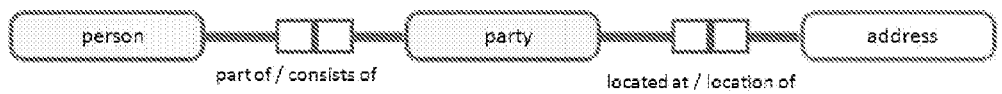
FIG. 10 illustrates a semantic pattern to express that persons are part of a certain party, and this party is located at a given address.

In a next embodiment said compound operators comprise atomic operators for moving relations. A move relation combines the insert and delete types described above. Consider the example illustrated in FIGS. 10 and 11. The semantic pattern of FIG. 10 explains that persons are part of a certain party, and that this party is located at a given address. The pattern has been committed with the following mappings:

map "/.../address"
on Address of Party.

It appeared that a mistake was made in designing the semantic pattern, because the address should actually be the location of the person being part of the party. This can be resolved using the following change log:

defineDifferentia("Person", "located at", "location of", "Address")
dropDifferentia("Party", "located at", "location of", "Address")

Figure 11:
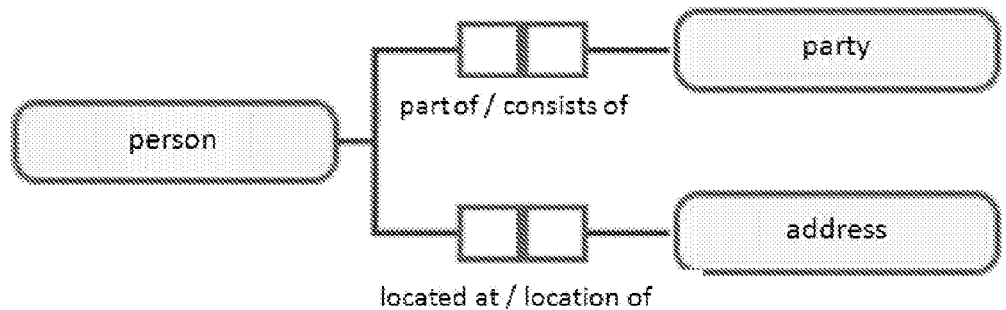
FIG. 11 illustrates the semantic pattern of FIG. 10 after applying a change log for moving relations.

The result is the semantic pattern of FIG. 11 and corresponding commitment:

map "/.../address"
on Address of Person.

The solution provided by the present invention is firstly the introduction of a compound operator for the semantic pattern that can be incorporated in the change log. The compound operator defines a specific sequence of atomic operators. Secondly, this compound operator needs to have an equivalent operator that operates on the mappings in the commitment(s). The new operator is defined as follows:

$move(X, r', r, Y, Z) \equiv$ $+defineDifferentia(X, r', r, Z) + dropDifferentia(X, r', r, Y)$ which looks as follows for the example:

$move(\text{"Address"}, \text{"location of"}, \text{"located at"}, \text{"Party"}, \text{"Person"}) \equiv$ $+defineDifferentia(\text{"Address"}, \text{"location of"}, \text{"located at"}, \text{"Person"}) +$ $dropDifferentia(\text{"Address"}, \text{"location of"}, \text{"located at"}, \text{"Party"})$ Concerning the mappings, the operator acts on the conceptual path part of the mappings:

map "/.../address"
on Address of Party.

The operator expresses that this conceptual path has been moved, and performs the operation map "/.../address"
on Address of Person.

Related to this is the new copy operator which is defined as follows:

$copy(X, r', r, Y, Z) \equiv$
$defineDifferentia(X, r', r, Z)$

Example 4

Conceptify

In a further embodiment said compound operators comprise atomic operators for adding concepts. The insert and delete types are hereby combined.

Figure 12:
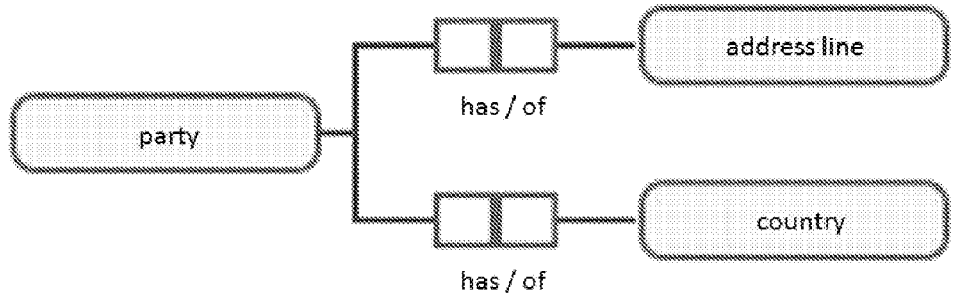
FIG. 12 illustrates a semantic pattern to express that a party has an address line and a country.
Figure 13:
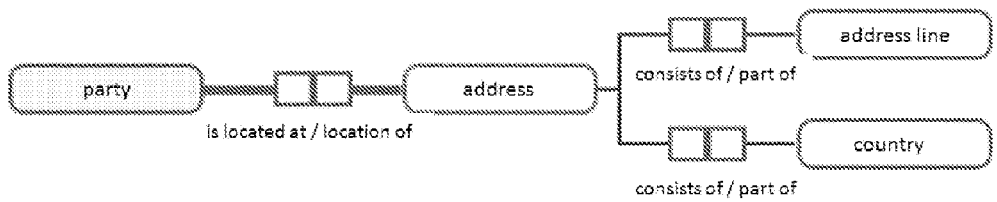
FIG. 13 illustrates the semantic pattern of FIG. 12 after applying a change log for adding a concept address consisting of an address line and country.

Consider the example illustrated in FIGS. 12 and 13. Considering the semantic pattern of FIG. 12 and the corresponding commitment:

map "/.../addressline"
on Address Line of Party.
map "/.../country_name"
on Country of Party.

Suppose country and address line need to be related via a new concept address. Address serves then as intermediate conceptualisation of the relation between country and address line; and party respectively.

This can be resolved using the following change log:

introduceTerm("Address")
defineDifferentia("Party", "is located at", "location of", "Address")
defineDifferentia("Address", "consists of", "part of", "Address Line")
dropDifferentia("Party", "has", "of", "Address Line")
defineDifferentia("Address", "consists of", "part of", "Country")
dropDifferentia("Party", "has", "of" "Address Line")

The result is the semantic pattern of FIG. 13 and corresponding commitment:

map "/.../addressline"
on Address Line part of Address location of Party.
map "/.../country_name"
on Country part of Address location of Party.

The solution provided by the present invention is firstly the introduction of a compound operator for the semantic pattern that can be incorporated in the change log. The compound operator defines a specific sequence of atomic operators. Secondly, this compound operator needs to have an equivalent operator that operates on the mappings in the commitment(s). The new operator is defined as follows:

$$conceptify(X, r'_0, r_0, Y, r'_n, r_n, Z_n) \equiv$$
$$introduceTerm(X)$$
$$defineDifferentia(X, r'_0, r_0, Y)$$
$$move(Z_n, r'_n, r_n, Y, X)$$

which looks as follows in the example:

*conceptify*("Address", "location of", "located at", "Party",

"has", "of", "Address Line", "has", "of", "Country") ≡

+*introduceTerm*("Address") +

*defineDifferentia*("Address", "location of", "located at", "Party") + move("Address Line", "of", "has", "party", "Address") + move("Country", "of", "has", "party", "Address")

Concerning the mappings, the operator acts on the conceptual path part of the mappings:

map "/.../addressline"
on Address Line of Party.

The operator expresses that this conceptual path has been moved, and performs the operation map "/.../address"
on Address Line of Address location of Party.

Example 5

Shortcircuit Concepts

In another embodiment said compound operators comprise atomic operators for removing concepts. Hereby the insert and delete type as describe above are combined.

Figure 14:
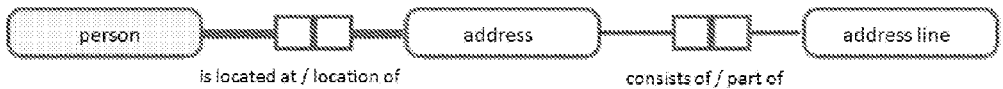
FIG. 14 illustrates a semantic pattern to express that a person has an address having an address line.
Figure 15:
FIG. 15 illustrates the semantic pattern of FIG. 14 after applying a change log for shortcircuiting the address concept.

Consider the example illustrated in FIGS. 14 and 15. Considering the semantic pattern of FIG. 14 and the corresponding commitment:

map /person/address/addressline
on Address Line of Address location of Person

Suppose the mapped path "Address Line of Address location of Person" needs to be simplified to "Address Line location of Person".
This can be resolved applying the following change log:

defineDifferentia("Person", "located at", "location of", "Address Line")
dropDifferentia("Address", "consists of", "part of", "Address Line")
dropDifferentia("Person", "located at", "location of", "Address")

The result is the semantic pattern of FIG. 15 and corresponding commitment:

map "/person/address/addressline"
on Address Line location of Person.

The solution provided by the present invention is firstly the introduction of a compound operator for the semantic pattern that can be incorporated in the change log. The compound operator defines a specific sequence of atomic operators. Secondly, this compound operator needs to have an equivalent operator that operates on the mappings in the commitment(s). The new operator is defined as follows:

$$shortcircuit(X, r_1 r'_1, Y, r_2, r'_2, Z) \equiv$$
$$+move(X, r_1, r'_1, Y, Z) + dropDifferentia(Y, r_2, r'_2, Z)$$

Which looks as follows in the example:

*shortcircuit*("Person", "located at", "location of",

"Address", "consists of", "part of", "Address Line") ≡

+move("Person", "located at", "location of",

"Address", "Address Line") +

*dropDifferentia*("Address", "consists of", "part of", Address Line")

Concerning the mappings, the operator acts on the conceptual path part of the mappings:

map "/.../addressline"
on Address Line of Address location of Person.

The operator expresses that this conceptual path has been moved, and performs the operation map "/.../address"
on Address Line location of Party.

Example 6

Basic Role Renaming

In yet another example said compound operators comprise atomic operators for renaming roles and/or co-roles. This is another case wherein the relabel type occurs.

Figure 16:
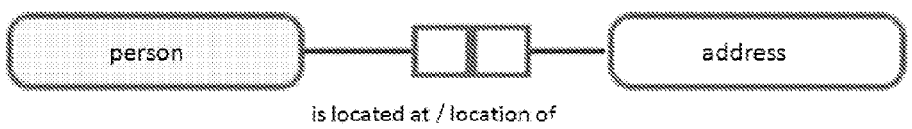
FIG. 16 illustrates a semantic pattern after applying a change log for the role/co-role for a person having an address into a person located at an address.

Consider the example illustrated in FIG. 16. The following pattern and mapping show the start situation:

map "/person/address"
on Address of Person.

To make the semantics of this pattern more clear, the following change log is executed, for instance, to make a difference with different kinds of locations: "Person born at/birthplace of Address", "Person domiciled at/domicile of Address", . . . .

dropDifferentia("Person", "has", "of", "Address")
defineDifferentia("Person", "located at", "location of", "Address")

The result of this change log is shown in of FIG. 16, requiring the following corresponding mapping:

map "/person/address"
on Address location of Person.

The solution provided by the present invention is firstly the introduction of a compound operator for the semantic pattern that can be incorporated in the change log. The compound operator defines a specific sequence of atomic operators. Secondly, this compound operator needs to have an equivalent operator that operates on the mappings in the commitment(s). The new operator is defined as follows:

$$renameDifferentia(X, r_1, r'_1, Y, r_2, r'_2) \equiv$$
$$+ dropDifferentia(X, r_1, r'_1, Y) + defineDifferentia(X, r_2, r'_2, Y)$$

which looks as follows for the example:

$$renameDifferentia(\text{"Person"}, \text{"has"}, \text{"of"}, \text{"Address"}, \text{"located at"},$$
$$\text{"location of"}) \equiv + dropDifferentia(\text{"Person"}, \text{"has"}, \text{"of"}, \text{"Address"}) +$$
$$defineDifferentia(\text{"Person"}, \text{"located at"}, \text{"location of"}, \text{"Address"})$$

Concerning the mappings, the operator acts on the conceptual path part of the mappings:

map "/person/address"
on Address of Person.

The operator expresses that this conceptual path has been renamed, and performs the operation map "/person/address"
on Address location of Person.

Example 7

Basic Term Renaming

In one embodiment said compound operators comprise atomic operators for renaming terms. Also here the relabel type is applied.

Consider the example illustrated in FIG. 12. The pattern of FIG. 12 and mapping show the start situation:

map "/.../addressline"
on Address line of Party.
map "/.../country_name"
on Country of Party.

To make the semantics of this pattern clearer, the following change log is executed:

dropDifferentia"Party", "has", "of", "Address Line")
dropDifferentia"Party", "has" ,"of", "Country")
defineDifferentia"Person", "has", "of", "Address Line")
defineDifferentia"Person", "has", "of", "Country")

Figure 17:
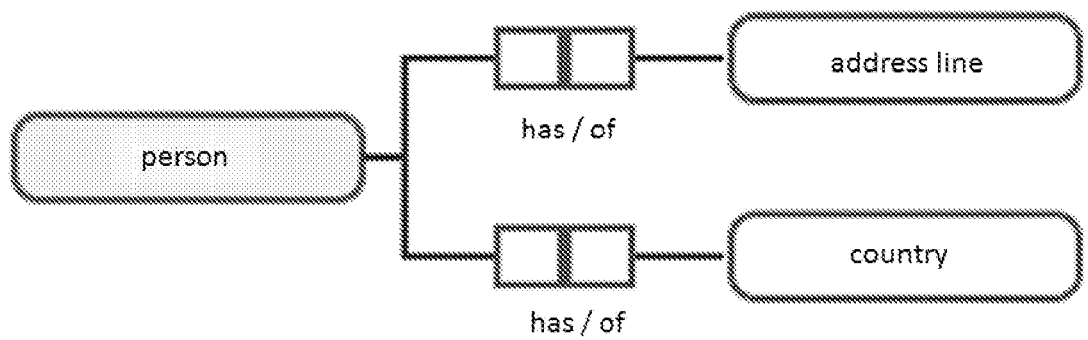
FIG. 17 illustrates the semantic pattern of FIG. 12 after applying a change log for renaming the term party by person.

The result of this change log is shown in FIG. 17.
And this requires the following corresponding mapping:

map "/.../addressline"
on Address Line of Person.
map "/.../country_name"
on Country of Person.

The solution provided by the present invention is firstly the introduction of a compound operator for the semantic pattern that can be incorporated in the change log. The compound operator defines a specific sequence of atomic operators. Secondly, this compound operator needs to have an equivalent operator that operates on the mappings in the commitment(s). The new operator is defined as follows:

$$renameTerm(X, Y) \equiv$$
$$+ introduceTerm(Y) + move(Z_n, r'_n, r_n, X, Y) + dropConcept(X) \text{ with}$$
$$(Z_n, r'_n, r_n,) \text{ being all relations attached to the original term } X.$$

which looks as follows in the example:

$$renameTerm(\text{"Party"}, \text{"Person"}) \equiv + introduceTerm(\text{"Person"}) +$$
$$move(\text{"Address Line"}, \text{"of"}, \text{"has"}, \text{"Party"}, \text{"Person"}) +$$
$$move(\text{"Country"}, \text{"of"}, \text{"has"}, \text{"Party"}, \text{"Person"}) +$$
$$dropConcept(\text{"Party"})$$

Concerning the mappings, the operator acts on the conceptual path part of the mappings:

map "/.../addressline"
on Address Line of Party.

The operator expresses that this conceptual path has been renamed, and performs the operation:

map "/.../addressline"
on Address Line of Person.
map "/.../country_name"
on Country of Person.

It must be noted that the data structure within the examples is specified in XML, but this may also be a database or any other data format, such as EDI, CSV or an SQL database. The methods of the present invention may be extended to any information system and any data format.

The systems and methods of the present invention may also apply for distributed ontology systems.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application.

The invention claimed is:

1. A computer implemented method comprising the steps of:
   detecting a change to one or more conceptual paths, each path addressing a part of a structure of an ontology system, the ontology system being an application-independent representation of domain knowledge by a set of concepts and relationships between the concepts, the change being described by an ordered sequence of first operators defining semantic information on said change, the change comprising appending another structure to part of the ontology system structure, said another structure not being part of the ontology system structure before the change;
   defining one or more second operators that operate on a mapping from at least one application path of an intentional part of a data system to a conceptual path of the ontology system, the intentional part being prescribed by constraints on data elements and relationships between the data elements, each application path addressing a part of the structure of the data system, said one or more second operators being equivalent to said one or more first operators used to describe said change to said one or more conceptual paths addressing said part of the structure of said ontology system; and
   updating said mapping with said one or more equivalent second operators to reflect the change to said one or more conceptual paths addressing said part of the structure of the ontology system.

2. The method as in claim 1, wherein said detected change is stored in a change log.

3. The method as in claim 1, comprising an initial step of applying said change to said ontology system.

4. The method as in claim 3, whereby one or more conditions are imposed for applying said change.

5. The method as in claim 1, wherein said change comprises a relabeling of part of the ontology system structure.

6. The method as in claim 1, wherein said change comprises inserting a further structure to a part of the ontology system structure, said further structure not being part of the ontology system structure before the change.

7. The method as in claim 1, wherein said change comprises deleting part of the ontology system structure.

8. A programmable device containing instructions, which, when executed, perform a method comprising steps of:
   detecting a change to one or more conceptual paths, each path addressing a part of a structure of an ontology system, the ontology system being an application-independent representation of domain knowledge by a set of concepts and relationships between the concepts, the change being described by an ordered sequence of first operators defining semantic information on said change, the change comprising appending another structure to part of the ontology system structure, said another structure not being part of the ontology system structure before the change;
   defining one or more second operators that operate on a mapping from at least one application path of an intentional part of a data system to a conceptual path of the ontology system, the intentional part being prescribed by constraints on data elements and relationships between the data elements, each application path addressing a part of the structure of the data system, said one or more second operators being equivalent to said one or more first operators used to describe said change to said one or more conceptual paths addressing said part of the structure of said ontology system; and
   updating said mapping with said one or more equivalent second operators to reflect the change to said one or more conceptual paths addressing said part of the structure of the ontology system.

9. A device comprising:
   means for detecting a change to one or more conceptual paths, each path addressing a part of a structure of an ontology system, the ontology system being an application-independent representation of domain knowledge by a set of concepts and relationships between the concepts, the change being described by an ordered sequence of first operators defining semantic information on said change, the change comprising appending another structure to part of the ontology system structure, said another structure not being part of the ontology system structure before the change;
   means for defining one or more second operators that operate on a mapping from at least one application path of an intentional part of a data system to a conceptual path of the ontology system, the intentional part being prescribed by constraints on data elements and relationships between the data elements, each application path addressing a part of the structure of the data system, said one or more second operators being equivalent to said one or more first operators used to describe said change to said one or more conceptual paths addressing said part of the structure of said ontology system; and
   means for updating said mapping with said one or more equivalent second operators to reflect the change to said one or more conceptual paths addressing said part of the structure of the ontology system.

10. The device as in claim 9, wherein said device is arranged to identify and store information on the version of said ontology system.

11. A computer implemented method comprising:
    detecting a change to a conceptual path addressing a part of a structure of an ontology system, the ontology system being an application-independent representation of domain knowledge by a set of concepts and relationships between the concepts, the change being described by an ordered sequence of first operators defining semantic information on said change, the change comprising appending another structure to part of the ontology system structure, said another structure not being part of the ontology system structure before the change;
    defining one or more second operators that operate on a mapping from at least one application path of an intentional part of a data system to the conceptual path addressing the part of the structure of the ontology system, the intentional part of the data system being prescribed by constraints on data elements and relationships between the data elements, the application path addressing a part of a structure of the data system, the one or more second operators being equivalent to the one or more first operators used to describe the change to the conceptual path addressing the part of the structure of the ontology system; and
    updating the mapping with the one or more equivalent second operators to reflect the change to the conceptual path addressing the part of the structure of the ontology system.

* * * * *